(12) United States Patent
Weber et al.

(10) Patent No.: US 6,420,604 B1
(45) Date of Patent: Jul. 16, 2002

(54) PROCESS FOR THE ACYLATION OF AMINO ALCOHOLS

(75) Inventors: Pieter Gijsbert Weber, Bn Ridderkerk; Erik De Vroom, Leiden, both of (NL)

(73) Assignee: Cosmoferm B.V. (NL)

( * ) Notice: Subject to any disclaimer, the term of this patent is extended or adjusted under 35 U.S.C. 154(b) by 0 days.

(21) Appl. No.: 09/462,348

(22) PCT Filed: May 7, 1999

(86) PCT No.: PCT/EP99/03250

§ 371 (c)(1),
(2), (4) Date: Jan. 7, 2000

(87) PCT Pub. No.: WO99/58542

PCT Pub. Date: Nov. 18, 1999

(30) Foreign Application Priority Data

May 14, 1998 (EP) .............................................. 98201647

(51) Int. Cl.$^7$ ........................ C07C 231/00; C07G 3/00; C07G 17/00

(52) U.S. Cl. ..................... 564/142; 564/143; 536/18.5; 536/18.6; 536/124

(58) Field of Search ................................ 564/142, 143; 536/18.6, 18.5, 124

(56) References Cited

U.S. PATENT DOCUMENTS 4,115,588 A * 9/1978 Kaminski et al. ............ 564/142
5,631,356 A * 5/1997 Smeets et al. ............. 536/18.6

FOREIGN PATENT DOCUMENTS

| EP | 212 400 | 1/1992 |
| WO | 93/20038 | 10/1993 |

* cited by examiner

Primary Examiner—Alan Siegel
(74) Attorney, Agent, or Firm—Morrison & Foerster LLP

(57) ABSTRACT

The present invention discloses an improved process for the N-acylation of amino alcohols employing an organic acid in the form of an acid halogenide, wherein the acylation occurs in an organic solvent in the additional presence of water.

12 Claims, No Drawings

PROCESS FOR THE ACYLATION OF AMINO ALCOHOLS

This application is a 371 of PCVEP99/03250 filed May 7, 1999.

FIELD OF THE INVENTION

The present invention relates to the field of acylation of amino alcohols.

BACKGROUND OF THE INVENTION

Ceramides are the main lipid component in the upper layer of the skin, the stratum corneum. This skin layer has an important barrier function in that external compounds generally are kept out whereas loss of moisture from the skin is limited. Ceramides are applied in cosmetics for instance because of their moisture retaining effects on the skin.

Typically, ceramides for use in cosmetics are obtained either from a natural source, via chemical synthesis routes or via a combined fermentative and chemical synthesis process. The latter routes are preferred due to the fact that potentially harmful infectious agents may be present in mammalian sources.

Various methods to synthesize ceramides are known in the art. The methods most frequently used involve a sphingoid base and a suitable fatty acid component as the starting materials. The fatty acid component is thereby coupled to the amino group of the sphingoid base via an amide linkage.

WO 93/20038 describes the acylation of amino alcohols whereby the fatty acid is coupled to the amino group as a mixed anhydride. It is essential for this reaction using a mixed anhydride that it occurs under essentially non-aqueous conditions.

Philippe et al. (Int. J. Cosm. Sci. 17, 133–146, 1995) describe an acylation method wherein the fatty acid is coupled to the amine as an acid halogenide, using tetrahydrofuran (THF) as the solvent and triethylamine as the organic base. In this method, the coupling reaction also occurs in a non-aqueous environment.

The requirement for non-aqueous conditions is an important disadvantage in those cases that one or both starting compounds are delivered as a water-containing material. For instance, in the case that the sphingoid base is contained within a wet crystal cake originating from a microbial fermentation process.

A further disadvantage of the above desribed methods is that they only result in a moderate product yield.

Still another acylation method is known applying a solvent system wherein THF is mixed with an equal volume of a 50% NaAc solution (see EP 212400). Although water is present in this system, the additional presence of a high salt concentration is required. A high salt concentration is undesired in that it is expensive and increases the waste load.

It is therefore desirable to be able to apply an acylation process wherein it is not required that the sphingoid base reactant is essentially water-free, which additionally does not require a high salt concentration and which gives a higher product yield than the currently known processes.

DESCRIPTION OF THE INVENTION

The present invention discloses a process for the acylation of an amino alcohol using a fatty acid being in the form of an acid halogenide, wherein the coupling occurs in an organic solvent in the additional presence of water.

The fact that water is present in the reaction mixture has several important advantages. For instance, it is not necessary to dry the amino alcohol reactant before applying the same in the acylation process. This is especially advantageous when the amino alcohol, e.g. a sphingoid base, is obtained via microbial fermentation or as a product from a reaction occurring in an aqueous environment. In addition, the pH of the process can be advantageously controlled using a simple mineral base, such as NaOH, instead of a potentially hazardous organic base.

The process of the invention further neither requires the use of a high salt concentration, as is the case for the process disclosed in EP 212400, nor the use of stoichiometric amounts of auxiliary chemicals, as is the case for the process disclosed in WO93/20038. A further important advantage is that the acylated reaction product is recovered from the organic phase by simply washing the organic phase with water followed by azeotropic removal of water and crystallization. Unexpectedly, the process of the invention provides an acylated amino alcohol in a yield which is considerably higher than the yields obtained in WO 93/20038 or by Philippe et al. In addition, the product has a high purity, i.e. does not contain undesired byproducts, since O-acylation occurs only to a very minor extent.

In the process of the invention, an amino alcohol is acylated with an organic acid of formula RCOOH, the organic acid being in the form of an acid halogenide, said process comprising the steps of:

- suspending or dissolving the amino alcohol, or a salt thereof, in an organic solvent in the presence of 0.01 to 10 volumes of water to one volume of organic solvent,
- adding the organic acid halogenide as a pure compound or as a solution or suspension in the organic solvent used to suspend the amino alcohol, while keeping the pH at a value of about 5 to 12,
- stirring the resulting mixture until the amino alcohol is converted to the N-acylated compound,
- recovering the N-acylated aminoalcohol from the organic phase.

In the organic acid of formula RCOOH, R is hydrogen, an optionally unsaturated, optionally substituted, optionally one or more heteroatoms containing straight chain or branched alkyl group having up to 55 carbon atoms; an optionally unsaturated, optionally substituted, optionally one or more heteroatoms containing $C_{5-8}$ cycloalkyl group; an optionally substituted aryl or heteroaryl group; or an optionally substituted benzyl group.

In a preferred embodiment of the invention, the alkyl group is optionally interrupted by an oxygen atom or by an internal ester group. In another preferred embodiment, the alkyl group has 1 to 50 carbon atoms, more preferably 10 to 50 carbon atoms, most preferably 15 to 45 carbon atoms.

A preferred substituent of the above defined groups is a hydroxyl group, especially an α-hydroxyl group.

In a preferred embodiment of the invention, the organic acid of formula RCOOH is hexanoic acid, octanoic acid, stearic acid, oleic acid, linoleic acid, 27-stearoyloxy-heptacosanoic acid, 27-linoleoyloxy-heptacosanoic acid, α-hydroxy-stearic acid, lactic acid, retinoic acid, salicylic acid or ferulic acid.

Protecting groups for the optional hydroxyl groups are well known in the art and may be selected from appropriate groups as disclosed in Greene, T. (1981) Protective Groups in Organic Synthesis (John Wiley & Sons; New York). In one embodiment of the invention, a hydroxyl group is protected as an acetyl ester or a methoxy methyl ether.

In another embodiment of the invention, a hydroxyl group is provided by first coupling an acid halogenide containing a halogen group at the position corresponding to the future hydroxyl group and subsequently converting the halogen group, i.e. after coupling, to an oxygen function, for instance an acetoxy group. Conversion of the halogen group into an oxygen function and subsequent conversion of the oxygen function into a hydroxyl group are conveniently performed using commonly known methods. Preferably, the halogen group is a bromine group.

The present invention also envisages the option to use a mixture of related organic acids, for instance a mixture of fatty acids having an alkyl group of different chain lengths and/or different extent of unsaturation.

In another preferred embodiment of the invention, the amino alcohol is a sphingoid base of formula

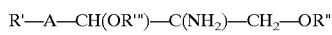

or a salt thereof, wherein:
- R' is a straight chain or branched alkyl group having 10 to 22 carbon atoms which may optionally contain one or more double bonds and/or may optionally be substituted, preferably with one or more hydroxyl groups, preferably is a straight chain alkyl group having 12 to 18 carbon atoms, more preferably is a straight chain alkyl group having 13 carbon atoms, and
- R" is hydrogen or a carbohydrate, such as a hexose or pentose moiety (optionally linked to further carbohydrate moieties), preferably hydrogen or a glucose or galactose moiety,
- A is $CH_2$—$CH_2$, CH=CH or $CH_2$—C(H)OR''', and R''' is hydrogen or an acyl group of 1 to 3 carbon atoms, preferably is hydrogen or an acetyl group.

The sphingoid base which is used in the method of the invention preferably is a sphingosine, a sphinganine or a phytosphingosine. More preferably, the sphingoid base is phytosphingosine.

In a especially preferred embodiment of the invention, phytosphingosine is obtained via deacetylation of tetraacetylphytosphingosine derived from a microbial fermentation, e.g. of the yeast *Pichia ciferri*. It is also possible to employ an acetylphytosphingosine obtained by partial deacetylation of tetraacetylphytosphingosine. The present invention advantageously allows that phytosphingosine or a partially deacetylated acetylphytosphingosine is directly used in the acylation process of the invention, without application of an intermittent recovery and/or drying step.

As salts of sphingoid bases, the HCl or sulphate salts are preferred.

The organic solvent which is employed in the coupling reaction can be any solvent resulting in a sufficient dissolution of the amino alcohol, i.e. a complete dissolution or a dissolution to an extent to keep the amino alcohol sufficiently susceptible to the subsequent reaction with the acid halogenide. Preferably, the organic solvent is a halogenated hydrocarbon, an ester, an ether, a ketone, an alkane, an aromatic hydrocarbon or an aromatic alcohol. More preferably, the organic solvent is a solvent which does not give rise to peroxide formation. Even more preferably, the organic solvent is not a solvent that is miscible with water in all mixing ratios. Even more preferably, the organic solvent is an alkyl ester of formic acid, acetic acid or propionic acid, the alkyl group being a methyl, ethyl, propyl, isopropyl, butyl or isobutyl group. Most preferably, the organic solvent is an alkyl ester of acetic acid, such as ethyl acetate, isopropyl acetate or butyl acetate. The use of alkyl esters of acetic acid has the advantage that these solvents are easily recovered from the process and optionally reused, are cheap and are no peroxide formers.

In the method of the invention, the amino alcohol is suspended in the organic solvent in the additional presence of water. The water can be added either during or after suspending the amino alcohol in the organic solvent, or can originate from the amino alcohol source, or both. The amount of water which may be present in the suspension or solution of the amino alcohol in the organic solvent conveniently may vary from 0.01 to 10 times the volume of the organic solvent. Preferably, the amount of water is 0.1 to 0.5 times the volume of the organic solvent. The upper limit of the amount of water generally will be determined by technical reasons, for instance by the volume of the reaction vessel.

The concentration wherein the amino alcohol is present in the organic solvent—water mixture conveniently may amount from 1 to 900 g/l, preferably from 25 to 250 g/l.

In a subsequent step in the process of the invention, the acid halogenide is added under stirring to the amino alcohol—organic solvent—water mixture, whereby the acid halogenide may be added as a pure compound or as a solution or suspension in the organic solvent used to suspend the amino alcohol.

In a preferred embodiment of the invention, the acid halogenide is an acid chloride.

The present invention also envisages the option to prepare the acid halogenide in situ by reacting an appropriate organic acid as defined above with a halogenating agent. Suitable halogenating agents are phosphorous trichloride or thionyl chloride.

The acid halogenide typically is added to the amino alcohol organic solvent—water mixture in an amount which is a molar equivalent of or which is a slight molar excess to the amount of amino alcohol.

While adding the acid halogenide to the amino alcohol—organic solvent—water suspension, the pH of the reaction mixture is kept at a value within a range of 5 to 12, preferably within a range of 6 to 11, by controlled addition of a base. The present invention advantageously allows that pH control is performed using a simple mineral base, such as NaOH. To keep the pH at a stable level during coupling, it is an option to add part of the base as sodium or potassium carbonate.

The temperature during the coupling reaction conveniently is held at a value to allow a thorough stirring of the mixture. The temperature during coupling may also depend on the boiling point of the solvent used. The higher this boiling point, the higher the temperature which may be applied. Typically, for preparation of N-acylated amino alcohols with a low solubility such as certain ceramides, the temperature is kept at a value of 40–80° C.

The reaction mixture is stirred for a sufficient time period to allow a substantially complete conversion of the amino alcohol to the N-acylated compound. The extent of conversion conveniently is checked by methods well known in the art, e.g. thin layer chromatography, NMR spectroscopy, HPLC, and the like. Typically, substantially complete conversion is obtained after a time period of about 30 to 60 minutes. In the case that no complete conversion is obtained, additional acid chloride may be added.

In one embodiment of the invention, a halogen substuent present in the R group of the organic acid RCOOH is converted into an oxygen function, subsequent to the coupling stage, in the same organic solvent as used in the coupling stage.

The N-acylated amino alcohol which is produced in the process of the invention is recovered from the organic phase using standard technology. The recovery process generally is a simple process, including washing of the organic phase with water and destining off the water-solvent azeotrope.

Briefly, after completion of the reaction, the temperature of the reaction mixture is increased to a value which is just below the boiling point of the mixture. The water layer is removed and the organic layer optionally is washed with water. The water-solvent azeotrope is distilled off. Optionally, a hot filtration step to remove solid particles and/or an active coal treatment for decolorization may be applied. The product is recovered from the organic phase by cooling and filtration of the crystalline product.

The N-acylated amino alcohol as prepared by the method of the invention preferably is a ceramide, a cerebroside, a retinoyl-sphingoid base, a salicyl-sphingoid base or a short-chain α-hydroxyacyl-sphingoid base. These compounds preferably are applied in cosmetic or dermatological compositions.

EXAMPLE 1

Preparation of N-Stearoyl-phytosphingosine

A suspension of 50 grams of phytosphingosine (purity 95.4%), 700 ml of isopropyl acetate and 100 ml of water was stirred under a nitrogen atmosphere in a jacketed 1 L reactor fitted with a mechanical stirrer, pH-electrode, refluxcondensor and nitrogen inlet, while keeping the reaction mixture at 50° C. by pumping water of 50° C. through the jacket. The pH was adjusted to 7.1 with 9.5 ml of 36% hydrochloric acid. During coupling, the pH was kept at 7+/−0.2 by the addition of 25% sodium hydroxide when required, by means of a pH-controlling system and a valve.

Over a period of 1¼ hour a mixture of 55 ml (48.42 g) of stearic chloride and 50 ml of isopropyl acetate was added from a dropping funnel while keeping the temperature at 50° C. A suspension was obtained. The dropping funnel was rinsed with 25 ml of isopropyl acetate. Stirring was continued at 50° C. for 0.5 hour. TLC (using chloroform/methanol ⅔ as the eluent and 5% phosphormolybdenic acid in ethanol for detection of lipids) showed that no phytosphingosine was present.

The mixture was heated to 77° C. by raising the water temperature to 80° C. and stirring was stopped to allow separation of the layers. The aqueous layer was removed together with some intermediate layer. The organic layer was stirred with 100 ml of water at 77° C. and the layers allowed to separate. The aqueous layer was combined with the first aqueous layer and extracted warm with 50 ml of isopropyl acetate. The organic layer was added to the first organic layer and the mixture was distilled off while returning the distillate to the reactor after removing the aqueous layer. After about 0.5 L of distillate the temperature of the liquid became 82° C. (vapour 72° C.) and 26 ml of water was removed.

The mixture was allowed to cool to 19° C. overnight while stirring gently and then filtered over a glass (G4) filter. The reactor was rinsed with 200 ml of isopropyl acetate in portions which was used to replace the filtercake. The filtercake was washed with another portion of 100 ml of isopropyl acetate and the wet filtercake (198 g) was dried under a stream of air at 35° C. Further drying under vacuum at 40° C. gave 87.5 g of N-stearoyl-phytospingosine. The yield was 91%.

EXAMPLE 2

Preparation of N-Stearoyl-phytospingosine

A suspension of 50 grams of phytosphingosine, 750 ml of isopropyl acetate and 100 ml of water was stirred under a nitrogen atmosphere in a jacketed 1 L reactor fitted with a mechanical stirrer, pH-electrode, refluxcondensor and nitrogen inlet, while keeping the reaction mixture at 50° C. by pumping water of 50° C. through the jacket. During the coupling stage, the pH was kept at 7 by the addition of 25% sodium hydroxide when required by means of a pH-controlling system and a valve.

Over a period of 1¾ hour a mixture of 55 ml (48.42 g) of stearic chloride and 50 ml of isopropyl acetate was added from a dropping funnel while keeping the temperature at 50° C. After adding about 40 ml of the mixture, the pH dropped to 7 and pH-control started. The dropping funnel was rinsed with 5 ml of isopropyl acetate. Stirring was continued at 50° C. for 0.5 hour and TLC showed that no phytosphingosine was present.

The mixture was heated to 76° C. by raising the water temperature to 80° C. and stirring was stopped to allow separation of the layers. The aqueous layer was removed together with some intermediate layer. The organic layer was stirred with 100 ml of water at 80° C. and the layers allowed to separate. The aqueous layer was extracted warm with 100 ml of isopropyl acetate. The organic layer was added to the first organic layer and the mixture was distilled off while returning the distillate to the reactor after removing the aqueous layer. After about 0.4 L of distillate the temperature of the liquid became 84° C. and 32 ml of water was removed.

The mixture was allowed to cool to 19° C. while stirring gently (crystallisation started at 78° C.) and then filtered over a glass (G3) filter. The reactor was rinsed with isopropyl acetate in portions which was used to replace the -filtercake (total of 300 ml). The wet filtercake (156 g) was dried under a stream of air at 35° C. Further drying under vacuum gave 88 g of N-stearoyl-phytospingosine with a purity of 98%. The yield was 98%.

EXAMPLE 3

Preparation of N-Oleoyl-phytosphingosine

A suspension of 50 grams of phytosphingosine, 750 ml of isopropyl acetate and 100 ml of water was stirred under a nitrogen atmosphere in a jacketed 1 L reactor fitted with a mechanical stirrer, pH-electrode, refluxcondensor and nitrogen inlet while keeping the reaction mixture on 50° C. by pumping water of 50° C. through the jacket. The pH was adjusted to 7 with 10 ml of 36% hydrochloric acid. During coupling stage the pH was kept at 7 by the addition of 25% sodium hydroxide when required, by means of a pH-controlling system and a valve.

Over a period of 1.25 hour a mixture of 55 ml of oleic chloride and 50 ml of isopropyl acetate was added from a dropping funnel while keeping the temperature at 50° C. The dropping funnel was rinsed with 5 ml of isopropyl acetate. Stirring was continued at 50° C. for 0.5 hour and TLC showed that no phytosphingosine was present.

The mixture was heated to 76° C. by raising the water temperature and stirring was stopped to allow separation of the layers. The aqueous layer was removed together with some intermediate layer. The organic layer was stirred with 100 ml of water at 76° C. and the layers allowed to separate. The mixture was distilled off while returning the organic layer of the distillate back into the reactor. After the temperature of the liquid became 84° C. the mixture was cooled to 12° C. while stirring gently (crystallisation started at 46° C.) and then filtered over a glass (G3) filter. The reactor was rinsed with isopropyl acetate in portions which was used to replace the filtercake (total of 300 ml).

The wet filtercake (224 g) was dried under a stream of air at 35° C. Further drying under vacuum at 40° C. gave 81.5 g of N-oleoyl-phytosphingosine with a purity of 98%. The yield was 91%.

EXAMPLE 4

Preparation of N-α-Hydroxystearoyl-phytosphingosine

A suspension of 50 grams of phytosphingosine sulphate, 500 ml of n-butyl acetate and 25 ml of water was stirred under a nitrogen atmosphere in a 1 liter 3-necked flask fitted with mechanical stirrer, ph-electrode, refluxcondesor and nitrogen inlet, while keeping the reaction mixture on 71° C.

During the coupling stage the pH was kept at 8.5 by the addition of 25% sodium hydroxide when required by means of a Mettler DL21 titrator. The mixture was pre-titrated with 11 ml of 25% NaOH to change the pH from ca 3.2 to ca 8. Next 2.7 grams of sodium carbonate were added and the pH changed to ca 9.

Over a period of ca 55 minutes a mixture of 50 ml (60 grams) of 2-bromo stearic chloride/bromide and 50 ml of n-butyl acetate was added from a dropping funnel causing the temperature to go to 75° C. A precipitate formed halfway the addition and the temperature was raised to 80° C. which improved solubility. Near the end of the addddition more precipitate was formed and the temperature was raised to 85° C. The dropping funnel was rinsed with 20 ml of n-butyl acetate. Stirring was continued at 85° C. for 1 hour.

Next the mixture was heated to reflux while separating the aqueous layer with a Dean-Stark setup and 78 ml of water layer was separated while the temperature went up to 130° C. After cooling to 116° C., 25 grams of anhydrous potassium acetate were added and the mixture was refluxed for 2 hours, temperature ca 129° C. After standing overnight at room temperature, refluxing was continued for another 1.5 hours.

Next the mixture was cooled to 100° C., 200 ml of water were added and the mixture was distilled off until the liquid temperature reached 106° C. During distillation a portion of 50 ml of water was added when 500 ml of distillate was collected. The distillate contained 165 ml of aqueous layer and 460 ml of organic layer. Next 500 ml of butanol and 100 ml of water were added and the mixture was heated to ca 88° C. After stirring stopped the aqueous layer was removed by suction and the organic layer was washed two more times with 100 ml of water at ca 90° C. The final water layer had a pH of 5.7 (volumes 150, 60 resp 80 ml). Next the pH was kept at 11 to 12 by the addition of 25% NaOH. The pH kept dropping. After ca 2 hours 12 ml of 25% NaOH were consumed., temperature was kept at ca 70–80° C. The stirring was stopped and 40 ml of aqueous layer was removed by suction. The organic layer was distilled off. During distillation two portions of butanol were added. A total of 190 ml of organic layer and 60 ml of aqueous layer of distillate were collected. The liquid temperature reached 108° C.

The mixture was cooled and at ca 46° C. precipitation started. Stirring and cooling was continued for 2 hours, end temperature was 2° C.

The precipitate was filtered off, and the cake was replaced with 250 ml of cold butanol and sucked dry (total ca 20 minutes).

The wet cake was heated in 500 ml of methanol, filtered while hot (70° C.) through a paper filter and washed with 25 ml of hot methanol. The filtrate was cooled and at ca 26° C. crystallisation started. Further cooled to 0° C. After stirring at 0° C. for 1 hour the precipitate was filtered off and the cake was replaced with 250 ml of cold methanol, fast filtration. The wet filtercake was dried under vacuum at 45° C. to give 60 g product.

EXAMPLE 5

Preparation of N-Octanoyl-phytosphingosine

A suspension of 50 grams of phytosphingosine sulphate, 525 ml of isopropyl acetate and 75 ml of demiwater was stirred under nitrogen in a jacketed 1 liter reactor fitted with mechanical stirrer, pH-electrode, refluxcondensor and nitrogen inlet while keeping the reaction mixture on 70° C. by pumping water of 70° C. through the jacket.

During the coupling stage the pH was kept at 8.5 by the addition of 25% w/w potassium hydroxide when required by means of a Mettler DL21 titrator. The initial pH of ca 4.5 was adjusted with 25% KOH to ca 7.5 and 3.16 g of potassium carbonate anh. were added, the pH became ca 8.1.

Over a period of ca ¾ hour a mixture of 20.55 g of octanoyl chloride and 37 ml of isopropyl acetate was added from a dropping funnel while keeping the temperature at 70° C. The dropping funnel was rinsed with 10 ml of isopropyl acetate. Stirring was continued at 70° C. After stirring for 0.5 hour, the presence of a small amount of phytosphingosine was detected by TLC and 1 ml of octanoyl chloride was added. After 0.5 hour phytosphingosine was still present and another 1 ml of octanoyl chloride was added. 10 minutes later the reaction was stopped and the mixture was kept overnight at room temperature.

The mixture was heated to 70° C. and another 0.5 ml of octanoyl chloride was added. After stirring for 15 minutes, stirring was stopped to allow separation of the layers, solids were present in the aquous layer which dissolved after adding 100 ml of water. After 10 minutes the aqueous layer was removed. The organic layer was stirred with 100 ml of water at 71° C. and allowed to separate. The aqueous layer was removed. The organic layer was distilled off while returning the organic layer of the distillate back into the reactor (Dean-Stark setup). When the temperature of the liquid reached 82.6° C. the water layer was 20 ml. The mixture contained 13.3 mg H2O/g.

Stirring was continued while cooling to 8° C. in ca ¾ hours, at ca 52° C. crystallisation started. Stirring was continued at 8° C. for 0.5 hour and the suspension was filtered over a glass filter (G3, width 10 cm). The reactor was rinsed with isopropyl acetate (total of 180 ml) in 3 portions which was used to replace the filter cake and the cake was sucked near dry. The wet filter cake was dried under vacuum to give 55 g product.

EXAMPLE 6

Preparation of N-Hexanoyl-phytosphingosine

A suspension of 50 grams of phytosphingosine sulphate, 525 ml of isopropyl acetate and 75 ml of demiwater was stirred under nitrogen in a jacketed 1 liter reactor fitted with mechanical stirrer, pH-electrode, refluxcondensor and nitrogen inlet while keeping the reaction mixture on 70° C. by pumping water of 70° C. through the jacket.

During the coupling stage the pH was kept at 8.5 by the addition of 25% w/w potassium hydroxide when required by means of a Mettler DL21 titrator. The initial pH of ca 4.5 was adjusted with 25% KOH to ca 7.5 and 3.16 g of potassium carbonate anh. were added, the pH became ca 8.1.

Over a period of ca ¾ hour a mixture of 19.26 g of hexanoyl chloride and 40 ml of isopropyl acetate was added from a dropping funnel while keeping the temperature at 70° C. The dropping funnel was rinsed with 10 ml of isopropyl acetate. Stirring was continued at 70° C. After stirring for 0.5 hour TLC showed no phytosphingosine and stirring was stopped to allow separation of the layers. Solids were present in the aqueous layer which dissolved after adding 50 ml of water. After 10 minutes the aqueous layer was removed. The organic layer was stirred with 100 ml of water at 71° C. and allowed to separate. The aqueous layer was removed. The organic layer was distilled off while returning the organic layer of the distillate back into the reactor (Dean-Stark setup). When the temperature of the liquid reached 82.6° C. the water layer was 20.5 ml. The solution was filtered while hot, rinsed with 40 ml of hot isopropyl acetate. The filtrate contained 11.8 mg H2O/g. This was kept over the weekend at room temperature.

The mixture was heated to 60° C. while stirring to obtain a solution. Stirring was continued while cooling and at 35° C. crystallisation started. Stirring and cooling was continued to 1° C. in ca 1 hour. After stirring was continued at 1° C. for 1 hour the suspension was filtered over a glass filter (G3, width 10 cm). The flask was rinsed with cold isopropyl acetate (total of 200 ml) in 3 portions which was used to replace the filtercake and the cake was sucked near dry, total filtration took ca 2.5 hours. The wet filtercake was dried under vacuum at 49° C. to give 51 g product.

What is claimed is:

1. A process for the preparation of an N-acylated amino alcohol comprising the N-acylation of an amino alcohol or a salt thereof with an organic acid of formula R—COOH, wherein R is hydrogen; an optionally unsaturated, optionally substituted, optionally one or more heteroatoms containing straight chain or branched alkyl group having up to 55 carbon atoms; an optionally unsaturated, optionally substituted, optionally one or more heteroatoms containing $C_{5-8}$ cycloalkyl group; an optionally substituted aryl or heteroaryl group; or an optionally substituted benzyl group, the organic acid being in the form of an acid halogenide, wherein the coupling (N-acylation) occurs in an organic solvent in the additional presence of water.

2. A process for the preparation of an N-acylated amino alcohol according to claim 1, comprising the steps of:

suspending or dissolving the amino alcohol, or a salt thereof, in an organic solvent in the presence of 0.01 to 10 volumes of water to one volume of organic solvent, adding the organic acid halogenide as a pure compound or as a solution or suspension in the organic solvent used to suspend the amino alcohol, while keeping the pH at a value of within a range of 5 to 12, stirring the resulting mixture until the amino alcohol is converted to the N-acylated compound, recovering the N-acylated amino alcohol from the organic phase.

3. The process of claim 2, wherein the pH is kept at a value of 6 to 11.

4. The process of claim 1, wherein the acid halogenide is produced in situ in the organic solvent.

5. The process of claim 1, wherein the acid halogenide is an acid chloride.

6. The process of claim 1, wherein a hydroxyl substituent on the N-acylgroup of the N-acylated amino alcohol is provided by a corresponding halogen substituent on the R group of the organic acid halogenide, said halogen substituent being converted into an oxygen function after coupling and said oxygen function subsequently being converted into the hydroxyl substituent.

7. The process of claim 1, wherein the organic solvent is a halogenated hydrocarbon, an ester, an ether, a ketone, an alkane, an aromatic hydrocarbon or an aromatic alcohol.

8. The process of claim 7, wherein the organic solvent is not a solvent that is miscible with water in all mixing ratios.

9. The process of claim 7, wherein the organic solvent is an alkyl ester of formic acid, acetic acid or propionic acid, the alkyl group being a methyl, ethyl, propyl, isopropyl, butyl or isobutyl group.

10. The process of claim 9, wherein the organic solvent is ethyl acetate, isopropyl acetate or butyl acetate.

11. The process of claim 1, wherein the amino alcohol is a sphingoid base of formula

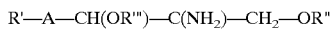

wherein:

R' is a straight chain or branched alkyl group having 10 to 22 carbon atoms which may optionally contain one or more double bonds and/or may optionally be substituted, preferably with one or more hydroxyl groups, preferably is a straight chain alkyl group having 12 to 18 carbon atoms, more preferably is a straight chain alkyl group having 13 carbon atoms, and R" is hydrogen or a carbohydrate, such as a hexose or pentose moiety (optionally linked to further carbohydrate moieties), preferably hydrogen or a glucose or galactose moiety, A is $CH_2$—$CH_2$, CH=CH or $CH_2$—C(H)OR''', and R''' is hydrogen or an acyl group of 1 to 3 carbon atoms, preferably is hydrogen or an acetyl group.

12. The process of claim 11, wherein the sphingoid base is a sphinganine, a sphingosine or a phytosphingosine.

* * * * *